(12) United States Patent
Iqbal et al.

(10) Patent No.: US 8,349,577 B2
(45) Date of Patent: Jan. 8, 2013

(54) METHOD FOR EVALUATING BLOOD-NEURAL BARRIER PERMEABILITY

(75) Inventors: Khalid Iqbal, Staten Island, NY (US); Sonia Chalbot, New York, NY (US); Inge Grundke-Iqbal, Staten Island, NY (US)

(73) Assignee: Research Foundation For Mental Hygiene, Inc., Menands, NY (US)

( * ) Notice: Subject to any disclaimer, the term of this patent is extended or adjusted under 35 U.S.C. 154(b) by 341 days.

(21) Appl. No.: 12/766,391

(22) Filed: Apr. 23, 2010

(65) Prior Publication Data

US 2010/0273196 A1    Oct. 28, 2010

(51) Int. Cl.
*C12Q 1/34* (2006.01)
(52) U.S. Cl. .......................... 435/18; 514/17.7
(58) Field of Classification Search .................... 435/18; 514/17.7
See application file for complete search history.

(56) References Cited

U.S. PATENT DOCUMENTS

| | | | |
|---|---|---|---|
| 5,552,530 | A | 9/1996 | Johnson et al. |
| 6,268,223 | B1 | 7/2001 | Cornell-Bell et al. |
| 6,514,984 | B1 | 2/2003 | Watanabe |
| 6,884,591 | B2 | 4/2005 | Janigro et al. |
| 7,144,708 | B2 | 12/2006 | Janigro et al. |
| 2002/0119139 | A1 | 8/2002 | Lazdunski et al. |
| 2003/0219849 | A1 | 11/2003 | Tsao et al. |
| 2005/0026235 | A1 | 2/2005 | Graham |
| 2006/0058225 | A1 | 3/2006 | David et al. |
| 2007/0249008 | A1 | 10/2007 | Mallat et al. |
| 2008/0119517 | A1 * | 5/2008 | Kristal et al. ................. 514/314 |
| 2008/0279846 | A1 | 11/2008 | Shi et al. |
| 2012/0142717 | A1 * | 6/2012 | Jin et al. ........................ 514/274 |

FOREIGN PATENT DOCUMENTS

| WO | WO 03069305 | 8/2003 |
|---|---|---|
| WO | WO 2008015546 | 2/2008 |

OTHER PUBLICATIONS

Chalbot S. et al. Cerebrospinal Fluid Secretory Ca2+ Dependent Phospholipase A2 Activity is Increased in Alzheimer Disease. Clinical Chemistry 55(12)2171-2179, Dec. 2009.*
Chalbot S. et al. Cerebrospinal Fluid Secretory Ca2+ Dependent Phospholipase A2 Activity. Neuroscience Letters 478(3)179-183, Jul. 12, 2010.*
Chalbot S. et al. Blood Cerebrospinal Fluid Barrier Permeability in Alzheimer's Disease. J of Alzheimer's Disease 25(3)505-515, 2011.*
Abbott, "Inflammatory Mediators and Modulation of Blood-Brain Barrier Permeability." 20 Cellular and Molecular Neurobiology, pp. 131-147 (2000).
Farooqui, et al., "Biochemical Aspects of Neurodegeneration in Human Brain: Involvement of Neural Membrane Phospholipids and Phospholipids A2." 29 Neurochemical Research, pp. 1961-1977 (2004).
Glasner, "Barrier Impairment and Immune Reaction in the Cerebrospinal Fluid." 13 European Neurology, pp. 304-314 (1975).
Radvanyi et al., "A Sensitive and Continuous Fluorometric Assay for Phospholipase A2 Using Pyrene-Labeled Phospholipids in the Presence of Serum Albumin." 177 Analytical Biochemistry, pp. 103-109 (1989).
Reiber et al., "Cerebrospinal Fluid Analysis: Disease-Related Data Patterns and Evaluation Programs." 184 Journal of the Neurological Sciences, pp. 101-122 (2001).
Reiber, "Dynamics of Brain-Derived Proteins in Cerebrospinal Fluid." 310 Clinica Chimica Acta, pp. 173-186 (2001).
Svensson et al., "Spinal Phospholipase A2 in Inflammatory Hyperalgesia: Role of the Small, Secretory Phospholipase A2." 133 Neuroscience, pp. 543-553 (2005).

* cited by examiner

*Primary Examiner* — Ralph Gitomer
(74) *Attorney, Agent, or Firm* — David L. Nocilly; Bond Schoeneck & King, PLLC

(57) ABSTRACT

A system and method for evaluating blood-neural barrier permeability. Phospholipid liposomes are labeled with a fluorescent phospholipase A2 substrate and exposed to cerebrospinal fluid. The change in fluorescence is monitored to determine PLA2 activity. The PLA2 activity is used to evaluate the permeability and function of the blood-neural barrier.

11 Claims, 16 Drawing Sheets

METHOD FOR EVALUATING BLOOD-NEURAL BARRIER PERMEABILITY

STATEMENT REGARDING FEDERALLY SPONSORED RESEARCH OR DEVELOPMENT

This invention was made with government support under grant number AG028538 awarded by the National Institutes of Health (NIH). The government has certain rights in the invention.

CROSS-REFERENCE TO RELATED APPLICATIONS

The present application claims priority to U.S. Patent Application Ser. No. 61/172,032, filed on Apr. 23, 2009, the entirety of which is hereby incorporated by reference.

BACKGROUND OF THE INVENTION

1. Field of the Invention

The present invention relates to evaluating the permeability of the blood-neural barrier, and, more specifically, to evaluating the permeability of the blood-neural barrier by measuring PLA2 activity in cerebrospinal fluid.

2. Description of the Related Art

Barriers between the peripheral circulation and neural tissues are collectively referred to as blood-neural barriers ("BNB") and include the blood-brain barrier ("BBB") and the blood-cerebrospinal fluid barrier ("BCB"), among others. The BBB and the BCB play critical roles in the transport of substances into and out of the brain and cerebrospinal fluid ("CSF"), respectively. Their main functions are to protect the brain from potentially harmful substances in the blood such as cytokines and drug metabolites, to ensure a constant supply of nutrients, and to regulate brain-borne substances in order to maintain brain homeostasis. Due to its essential role in the maintenance of normal brain function, the integrity of the BNB is strictly regulated in part by tight junctions, localized between cerebral endothelial cells for the BBB and between choroid epithelial cells for the BCB, that form an almost impermeable barrier.

Disruption of the tight junction architecture or dysregulation of transporters can result in increased permeability of the BNB and can contribute to the pathophysiology of several brain disorders including neurodevelopmental diseases such as autism, schizophrenia, epilepsy and cerebral palsy; neurological lesions caused by ischemia or trauma; multiple sclerosis; and neurodegenerative disorders such as Alzheimer's disease and Parkinson's disease.

As a result, predictable and reliable ways to assess BNB permeability are useful for analyzing central nervous system disorders and to monitor time-dependent response to therapies that target BNB disruption. Moreover, associated with other measurements the BNB integrity evaluation might facilitate the differential diagnosis of neurodegenerative disorders or identify potential therapeutic windows to increase the accessibility and efficacy of therapeutic treatments.

A number of techniques have been created to assess the permeability of the BNB. For example, imaging approaches such as gadolinium enhancement in T1-weighted magnetic resonance imaging (MRI) scans are used to assess BBB impairment. This assessment, however, requires both intravenous administration of the potentially toxic compound gadolinium as well as highly specialized and expensive equipment and expertise. Other strategies take advantage of the fact that any disruption in the BNB integrity allows protein leakage in both directions and evaluation of permeability using either a blood-specific protein or a brain-specific protein such as albumin or S100β, respectively. The most common and well-established method to evaluate BNB permeability is the measurement of the ratio of serum albumin in CSF ("$Q_{Alb}$"). In normal adult individuals, the $Q_{Alb}$ measurement is usually in the range of 6.8 to 10.2.

Despite the use of $Q_{Alb}$ to evaluate BNB permeability, new methods are needed to increase reliability and reproducibility, and especially to increase assay sensitivity. With increased reproducibility and sensitivity, BNB permeability assays will allow researchers to, among other things, (i) identify neurologic disorders which are not currently associated with BNB impairment; (ii) increase the specificity of differential diagnosis between neurodegenerative disorders; (iii) monitor time-dependent response to therapies that target BNB disruption as well as disease progression; and (iv) identify potential therapeutic windows in order to increase drug efficacy.

A possible candidate protein for improved evaluation of BNB permeability is phospholipase. The phospholipase A2 (PLA2) family of isozymes catalyze the hydrolysis of the sn-2 ester bond of glycerophospholipids, resulting in the production of free fatty acids (e.g. arachidonic acid and docosahexaenoic acid) and lysophospholipids. The free fatty acids and lysophospholipids metabolites created by PLA2 enzymatic activity can serve as precursors for the synthesis of proinflammatory mediators such as eicosanoids (prostaglandins and leukotrienes) and platelet activating factor and can induce the expression of chemokines and cytokines. As a result, PLA2s are considered key inflammatory enzymes.

The secretory $Ca^{2+}$-dependent phospholipases (sPLA2) are a member of the PLA2 family. The ten sPLA2 isozymes, which have been identified in many types of mammalian cells including the central nervous system, differ from other PLA2 enzymes by their low molecular weight, their requirement for millimolar calcium concentrations for catalytic activity, and their low selectivity for a specific phospholipid. Functionally, while the contribution of sPLA2 to various aspects of inflammation are well-documented, their involvement in BCB function has not been reported.

BRIEF SUMMARY OF THE INVENTION

It is therefore a principal object and advantage of the present invention to provide an improved assay for evaluation of blood-neural barrier permeability.

It is another object and advantage of the present invention to provide a method for a simple, reproducible, and sensitive assay to measure PLA2 activity in cerebrospinal fluid.

It is yet another object and advantage of the present invention to provide a method for evaluating blood-neural barrier permeability by utilizing a PLA2 activity assay.

In accordance with the foregoing objects and advantages, the present invention provides a method for evaluating the permeability of a blood-neural barrier. First, a quenched fluorescently labeled phospholipase substrate is exposed to a sample of cerebrospinal fluid. At least one of the phospholipases in the cerebrospinal fluid acts on the substrate and changes the fluorescence of the label. The change of the fluorescence in response to the cerebrospinal fluid sample is measured, and is correlated to the permeability of the blood-neural barrier.

In a second aspect of the present invention, the substrate is a liposome labeled with 1,2-bis-(4,4-difluoro-5,7-dimethyl-4-bora-3a,4a-diaza-s-indacene-3-undecanoyl)-sn-glycero-3- phosphocholine, and the phospholipase in the cerebrospinal fluid that acts on the label is a secretory $Ca^{2+}$-dependent phospholipase.

In a third aspect of the present invention, the step of correlating the change in the fluorescence to the permeability of the blood-neural barrier is accomplished by comparing the change in the fluorescence to the change caused by cerebrospinal fluid obtained from healthy individuals.

The present invention further provides a method of diagnosing impaired permeability of a patient's blood-neural barrier from a sample of cerebrospinal fluid taken from the patient. First, a quenched fluorescently labeled phospholipase substrate is exposed to a sample of cerebrospinal fluid. At least one of the phospholipases in the cerebrospinal fluid acts on the substrate and changes the fluorescence of the label. The change of the fluorescence in response to the cerebrospinal fluid sample is measured, and is correlated to the permeability of the blood-neural barrier. Lastly, the presence of impaired permeability of the patient's blood-neural barrier is diagnosed based on the change of the fluorescence.

In yet another aspect of the present invention, the presence of impaired permeability of the patient's blood-neural barrier is used to diagnose a neurological disorder in the patient.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

The present invention relates to a method of evaluating BNB permeability. Specifically, characterization of sPLA2 enzyme activity in CSF analyzes the permeability of the BNB. The present invention provides a method for measuring PLA2 activity in CSF using a format that allows for high-throughput analysis of samples. In a preferred embodiment, the fluorescence-based assay uses Bis-BODIPY® FL $C_{11}$-PC or a compound with similar properties as a substrate for the analysis of PLA2 activity. For the PLA2 assay, liposomes comprising phospholipids with DOPC are labeled with the Bis-BODIPY® FL $C_{11}$-PC.

The invention also provides a method for measuring secretory $Ca^{2+}$-dependent PLA2 activity in lumbar CSF using Bis-BODIPY® FL $C_{11}$-PC or a compound with similar chemical properties. The PLA2 activity in lumbar CSF was strongly inhibited by thioetheramide-PC (a competitive inhibitor of sPLA2) but not by $AACOCF_3$ (a specific inhibitor of cPLA2/iPLA2) or BEL (an inhibitor of iPLA2), suggesting that the PLA2 activity in lumbar CSF is predominately due to sPLA2 type.

The invention further provides a method for measuring CSF sPLA2 activity that is a more sensitive measure of BNB impairment (and particularly BCB function) than the traditional $Q_{Alb}$ measurement. The sPLA2 assay is easier and more sensitive than the $Q_{Alb}$ assay.

The following examples, which are provided by way of illustration, will further explain the sPLA2 assay and its use to evaluate BNB permeability but are not intended to limit the present invention.

Example 1

To measure PLA2 activity in human CSF, a continuous fluorescence assay using an already well-known PLA2 specific substrate—self-quenched fluorescent Bis-BODIPY® FL $C_{11}$-PC (also known as 1,2-bis-(4,4-difluoro-5,7-dimethyl-4-bora-3a,4a-diaza-s-indacene-3-undecanoyl)-sn-glycero-3-phosphocholine)—has been developed. Once incorporated into artificial cell membranes such as liposomes, the two BODIPY fluorophores added to the sn-1 and sn-2 acyl chains of phosphatidylcholine liberate attenuated fluorescence due to energy transfer between the BODIPY fluorophores. Upon cleavage by PLA2, the BODIPY from the sn-2 acyl chain is released and an increase in fluorescence can be measured due to the separation of the two BODIPY moieties. It should be noted, however, that one skilled in the art would recognize that the assay could employ any substrate that produces a measurable product in response to PLA2 in human CSF.

Figure 1A:
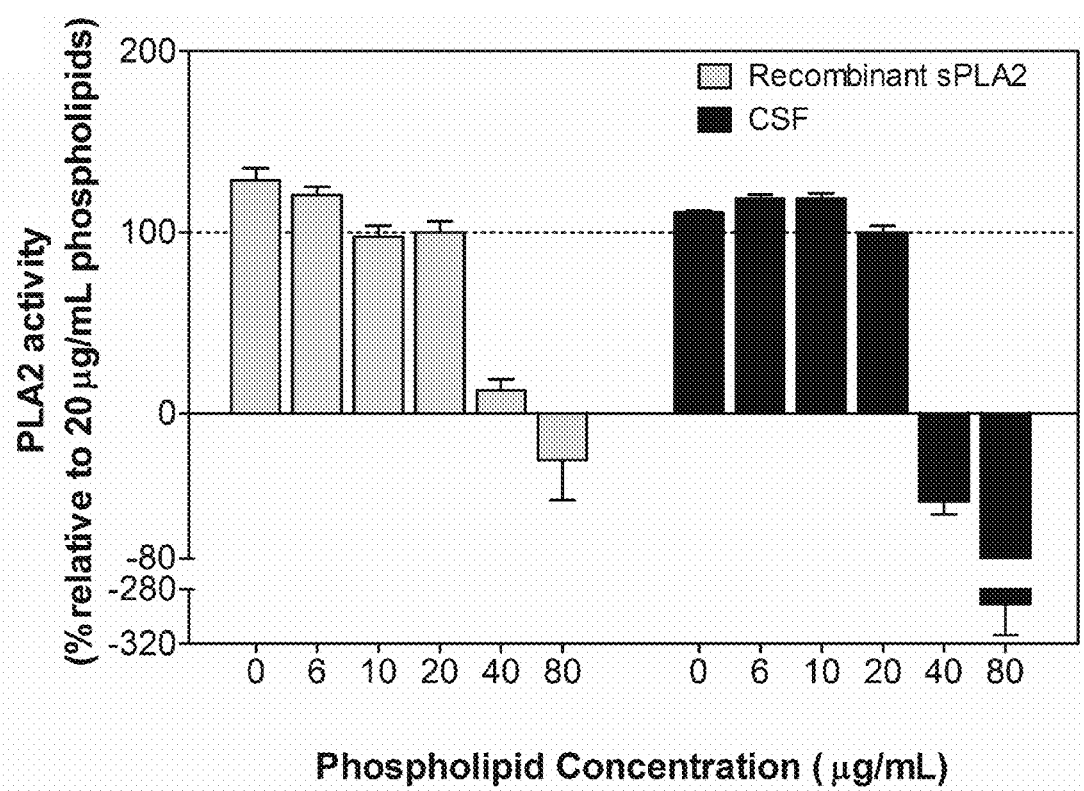
FIGS. 1A and 1B are graphs of the effect of liposome phospholipid concentration and composition on recombinant sPLA2 activity and CSF-derived PLA2 activity.
Figure 1B:
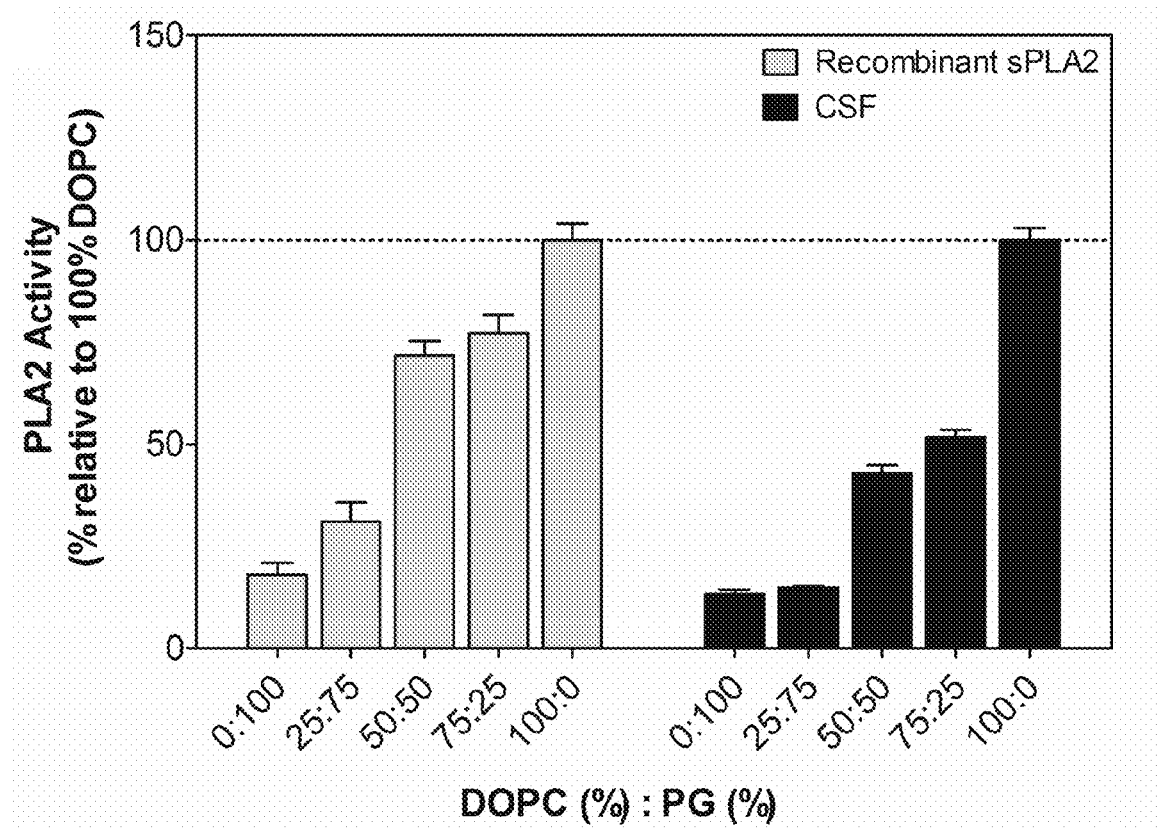
Figure 2A:
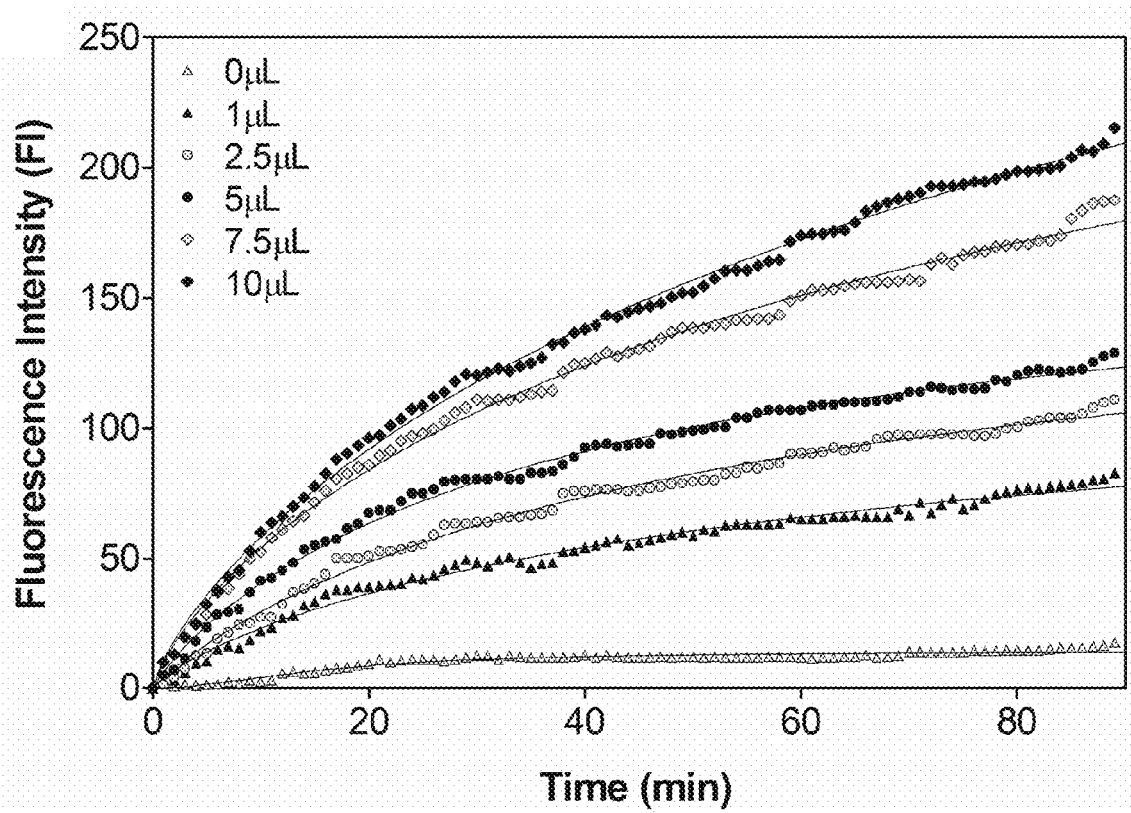
FIGS. 2A-2D are a series of graphs of the time-dependence of PLA2 activity using different volumes of lumbar CSF as well as the signal-to-concentration linearity performance and % coefficient of variation for repeatability and intermediate precision assessment for recombinant sPLA2 and CSF sPLA2.

Since it has previously been reported that PLA2 activity was dependent on phospholipid concentration and composition from liposomes, the effect of these two parameters on CSF activity and recombinant sPLA2 activity was assessed. A maximum rate of the enzymatic reaction was observed for both CSF and sPLA2 with liposomes made from 20 µg/mL 100% DOPC and labeled with 5 µM Bis-BODIPY® FL $C_{11}$-PC, as shown in FIGS. 1A-1B. Under these conditions, a time-dependent increase in fluorescence intensity ("FI") from lumbar CSF could be detected, while Bis-BODIPY® FL $C_{11}$-PC-labeled 100% DOPC liposomes alone did not cause an increase, as shown in FIG. 2A. Since there was no artifactual change in FI associated with the substrate, the observed changes in FI during the reaction can be associated to an enzymatic hydrolysis of Bis-BODIPY® FL $C_r$-PC by CSF PLA2 which produces fluorescence-labeled free fatty acid and lysophosphatidylcholine. Similar results were obtained with recombinant sPLA2.

Figure 2B:
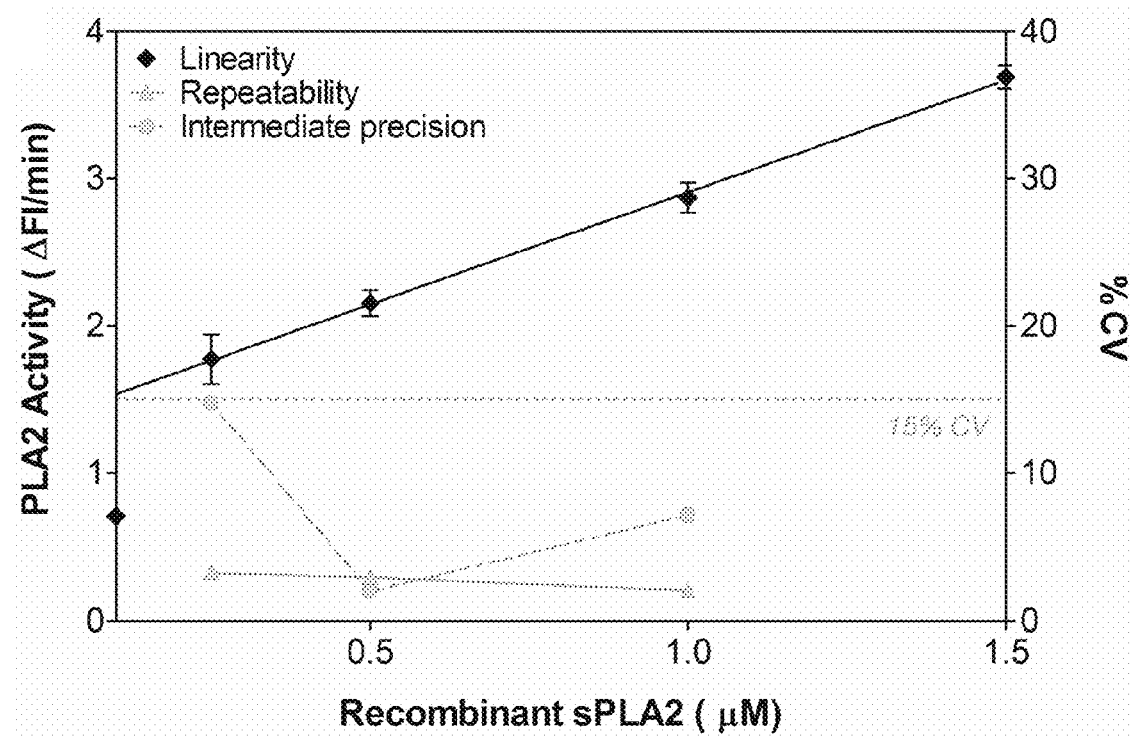
Figure 2C:
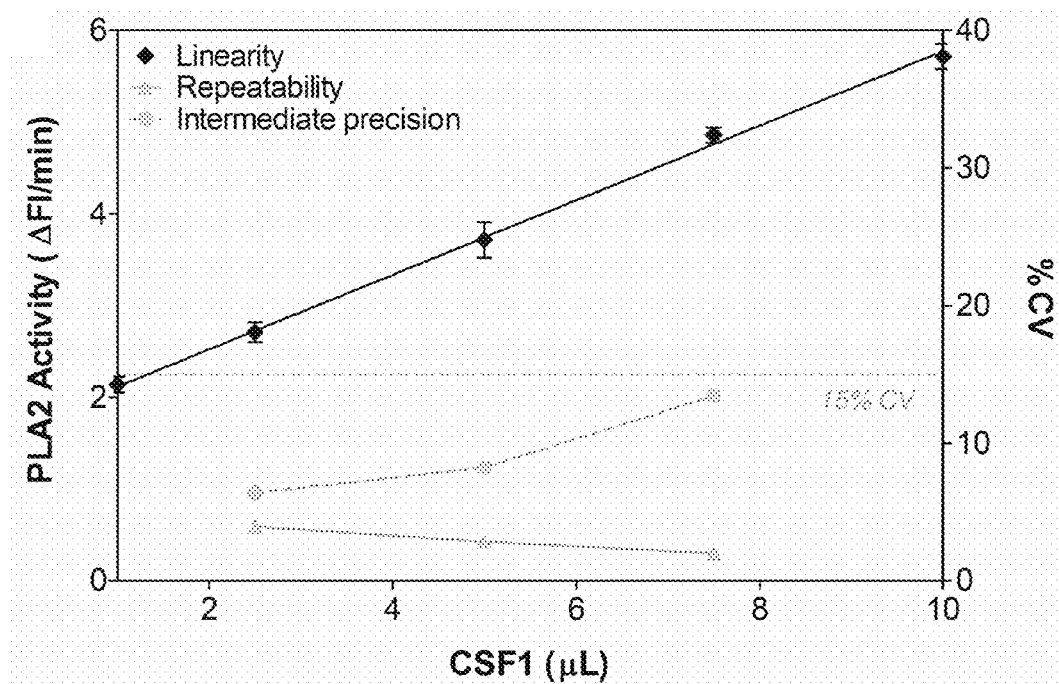
Figure 2D:
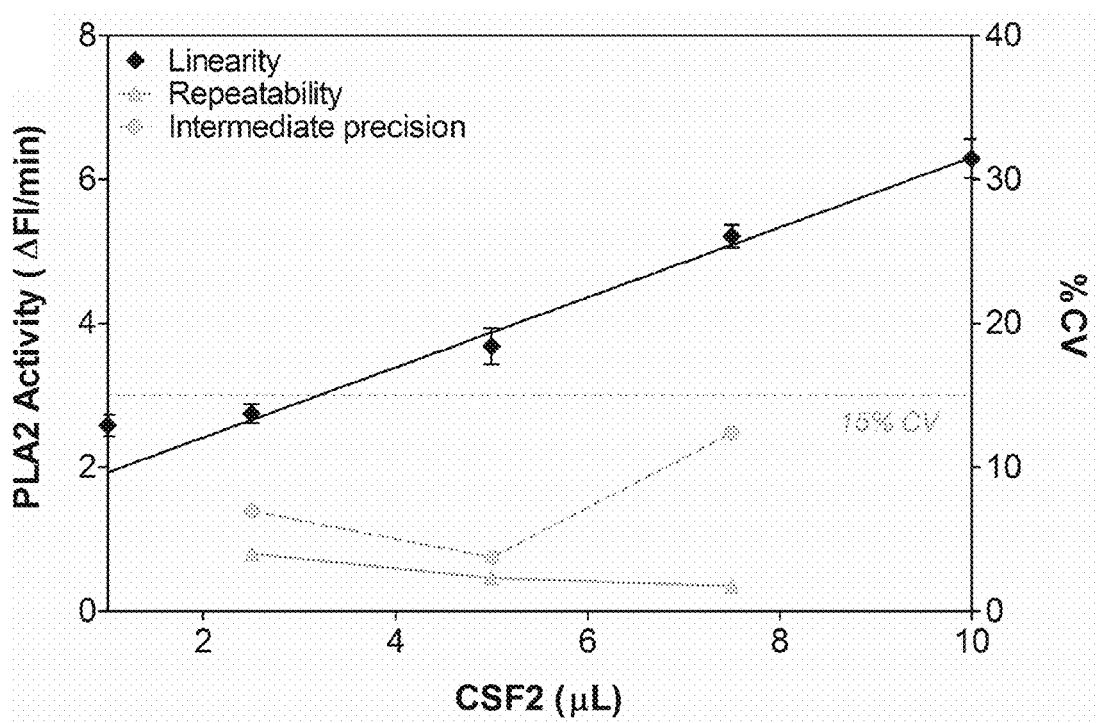

The new continuous fluorescence assay was validated using both recombinant sPLA2 (FIG. 2B) and lumbar CSF (FIGS. 2C and 2D). The performance of the assay provided conclusive results with less than 15% of coefficient of variation. The % CV range for precision was 2.0-14.8% for recombinant sPLA2 used from 0.25 to 1 µM and 1.8-13.4% for two different CSF samples used from 2.5 to 7.5 µL per assay. Moreover, the initial rate of reaction was dependent on recombinant sPLA2 concentration (FIG. 2B) and on CSF volume (FIGS. 2C and 2D) giving a recombinant sPLA2 signal-to-concentration linearity over the range 0.25 to 1.5 µM ($r^2=0.999$, $p<0.001$) and a linear signal-to-CSF volume relationship over the range 2.5 to 10 µL for the CSF1 ($r^2=0.997$, p=0.001) as well as for the CSF2 ($r^2=0.992$, p=0.004) tested.

Fluorescence-labeled liposomes were prepared similarly to a previously described method. To optimize the conditions for the measurement of PLA2 activity in CSF, parameters such as concentration and composition of phospholipids were adjusted. Briefly, 388 µg of DOPC and 97 nmoles of Bis-BODIPY® FL $C_{11}$-PC were mixed in 970 µL of chloroform. After drying under vacuum, 9701 µL of sucrose/Tris buffer (50 mM Tris-HCl, pH 7.4; 250 mM sucrose; 0.02% sodium azide) was added to it, followed by thorough and repeated mixing with a Vortex over 5 min at room temperature. The suspension was then ultrasonicated for 10 min on ice using an ultrasonic cell disrupter (Branson® Digital Sonifier®, Branson Instruments, Inc., Danbury, Conn.) at 50 W sonic energy. The liposomes were stored at −20° C. until used. Liposomes containing other proportions and/or types of phospholipids were prepared by comparable procedures.

PLA2 activity assays were carried out in triplicates using a continuous fluorescent measurement. In a 96-well microplate, 5 µL lumbar CSF (or 10 µM recombinant sPLA2) was diluted in 90 µL PLA2 assay buffer (10 mM Tris-HCl, pH 7.4; 100 mM KCl; 5 mM $CaCl_2$; 1 mM DTT). Then, 5 µL Bis-BODIPY® FL $C_{11}$-PC-labeled 100% DOPC liposomes were added to each well and the microplate was immediately placed in a temperature controlled (30° C.) cytofluor multi-well plate reader series 4000 (PerSeptive Biosystems®, Foster City, Calif.). The fluorescence intensity was recorded over 90 min (91 cycles of 60 sec each) at 485 nm excitation and 530 nm emission. Finally, PLA2 activity was evaluated using linear curve fitting with Graph Prism 3.0 (GraphPad Software™, San Diego, Calif.).

The linearity of the assay was assessed by measuring in triplicates the PLA2 activity at five different concentrations of recombinant sPLA2 (0-2 µM) as well as five different CSF volumes (0-10 µL). The precision was estimated by measuring repeatability and intermediate precision. Both measurements were assessed with three different concentrations of recombinant sPLA2 (0.25, 0.5 and 1 µM) as well as with three different CSF volumes (2.5, 5 and 7.5 µL). The repeatability was calculated by measuring PLA2 activity in sextuplicates. In order to evaluate the intermediate precision, each sample was analyzed three times a day on three consecutive days.

Example 2

Figure 3A:
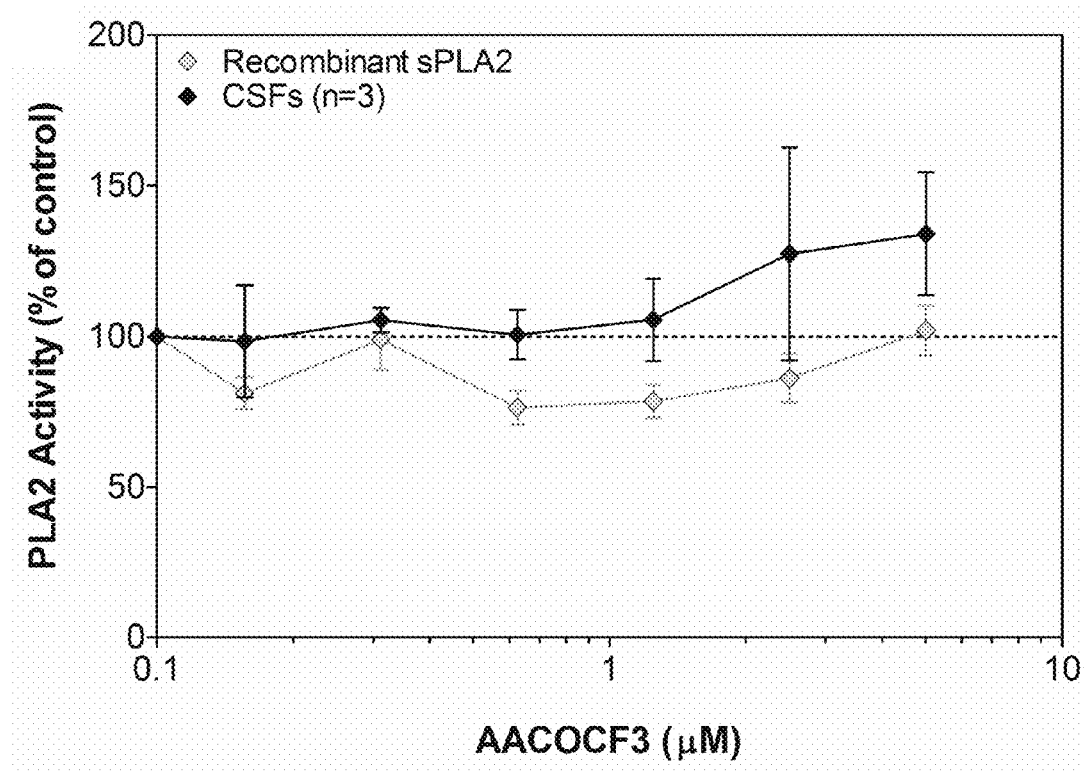
FIGS. 3A-3D are a series of graphs showing the effect of the PLA2-specific inhibitors $AACOCF_3$, BEL, and thioetheramide-PC and of calcium on recombinant and lumbar CSF-derived PLA2 activity.
Figure 3B:
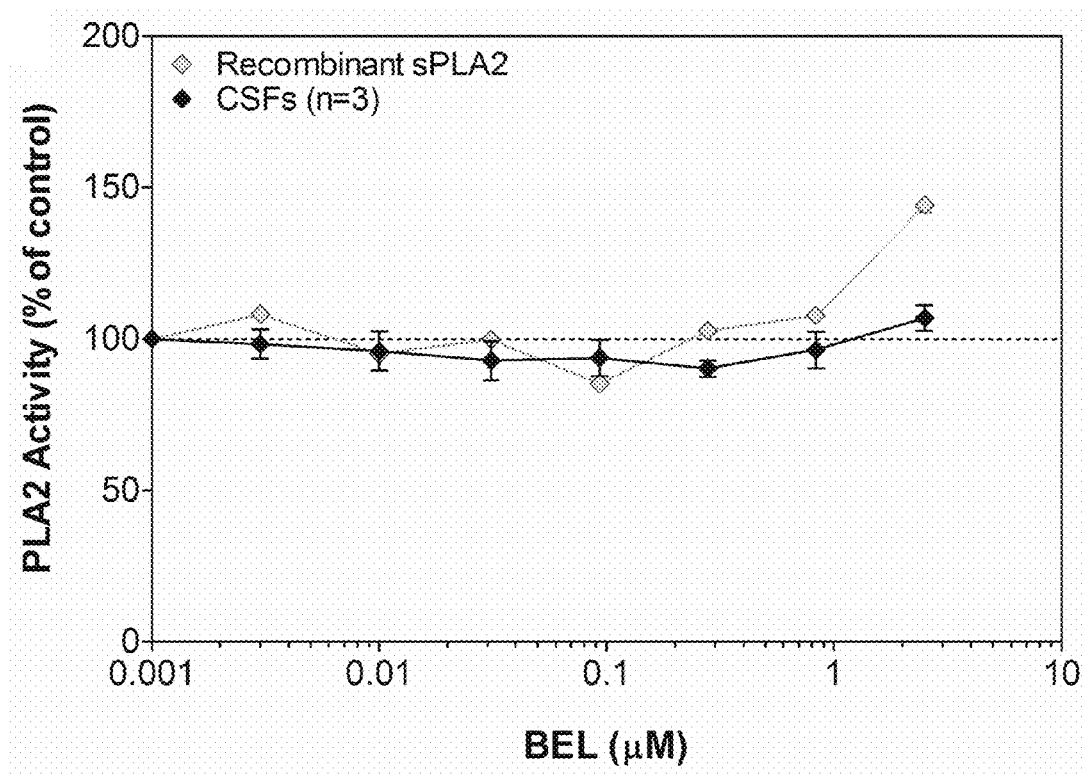
Figure 3C:
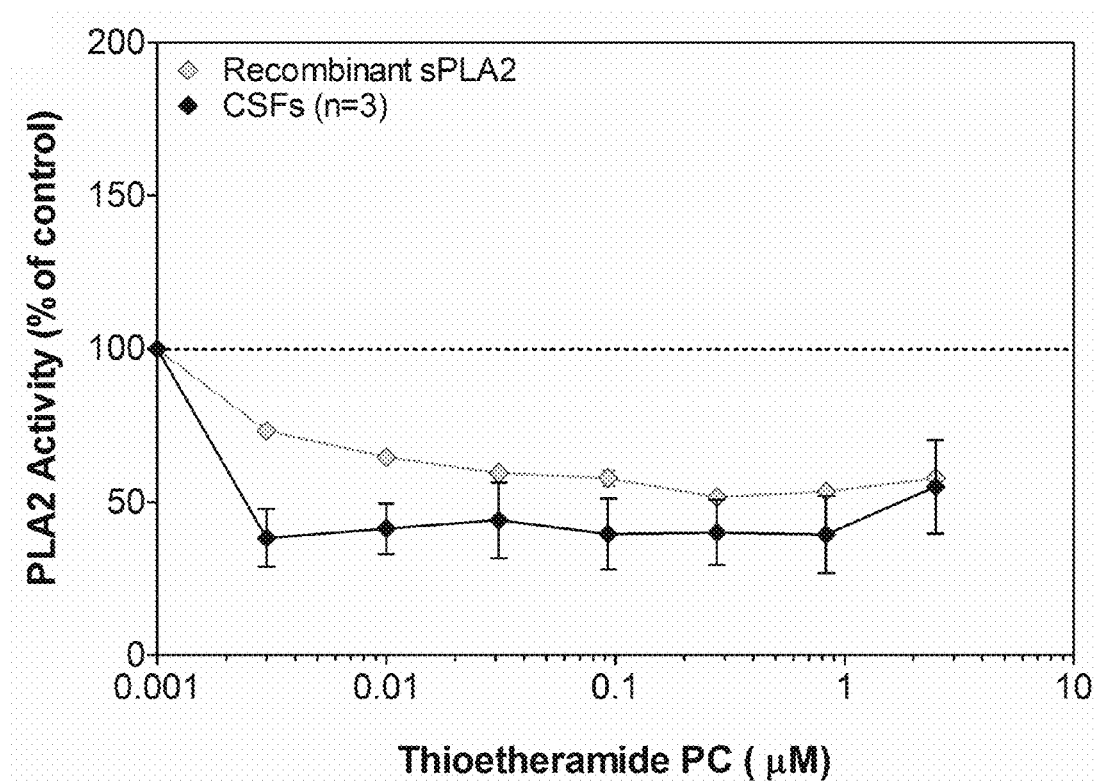

Although there are currently twenty-two different PLA2 enzymes classified in five families (sPLA2, cPLA2, iPLA2, PAF-AH and lysosomal PLA2), there is currently no known tool for the specific characterization of each of these isozymes. Thus, to characterize the activity of each new PLA2 the current approach is to determine to which family the PLA2 enzyme belongs. For this purpose, a battery of inhibitors more or less specific against each PLA2 family is generally used to discriminate one family from another. To identify the type of the PLA2 activity in the CSF measured using the assay developed in EXAMPLE 1, 5 µL of lumbar CSF was incubated in the presence of three different PLA2 inhibitors, $AACOCF_3$, BEL, and thioetheramide-PC, which are known to exhibit different relative potencies for the three major families of the enzyme (sPLA2, cPLA2 and iPLA2). $AACOCF_3$ is a selective inhibitor of both cPLA2 and iPLA2, BEL specifically inhibits isozymes from the iPLA2 family, and thioetheramide-PC functions as a competitive inhibitor of sPLA2. The pharmacological profile of the PLA2 activity in lumbar CSF was found to be most consistent with the sPLA2 subtype, as shown in FIGS. 3A-3C. While the sPLA2-specific inhibitor thioetheramide-PC dose-dependently inhibited the PLA2 activity from lumbar CSF as well as from the recombinant sPLA2 (FIG. 3C), the two other inhibitors failed to do so (FIGS. 3A and 3B).

Figure 3D:
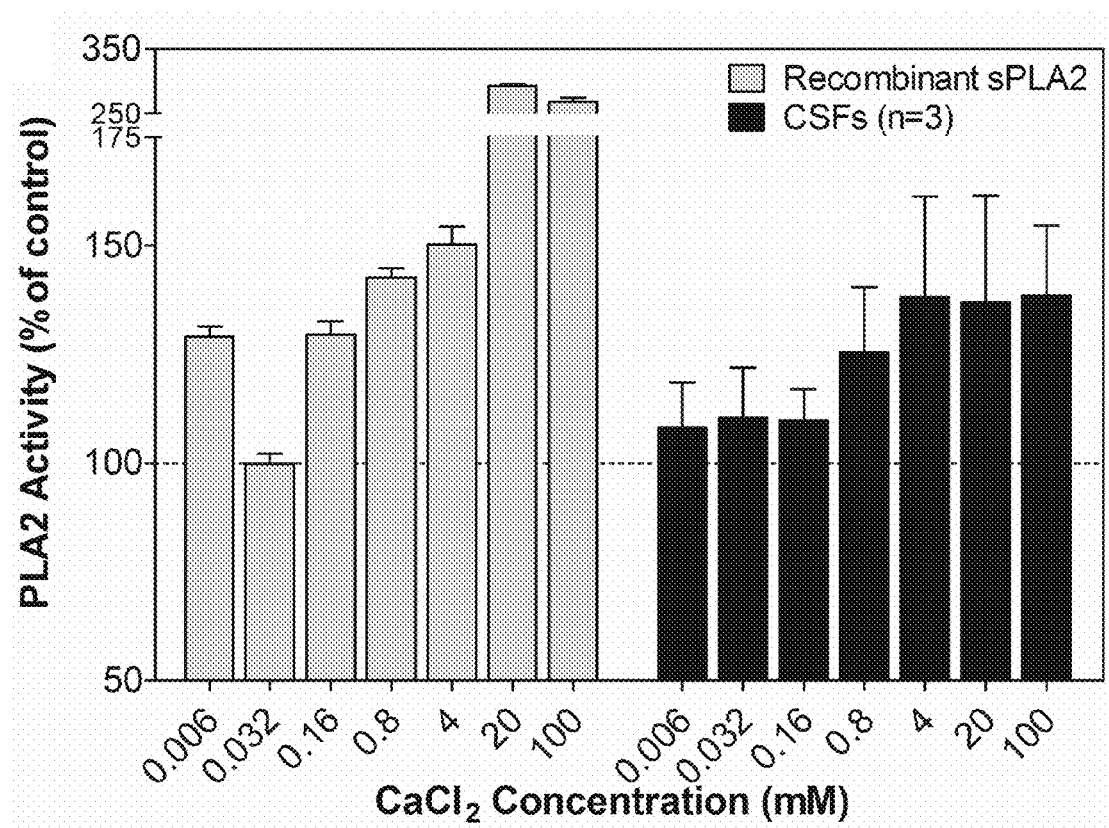

Calcium is required for the activity of both sPLA2 and cPLA2, although the role of calcium in the activation of each enzyme is different. While calcium resides at the catalytic center of sPLA2 and is directly involved in substrate-enzyme interaction, it is not required for cPLA2 catalytic activity but rather is involved in the translocation of cPLA2 from cytosol to the membrane where the substrates are located. To further characterize the CSF PLA2 and to confirm its type, PLA2 activity in the presence of various concentrations of calcium was assessed. When the concentration of calcium was increased, there was an increase of PLA2 activity in lumbar CSF as well as with recombinant sPLA2, as shown in FIG. 3D. As a result, the PLA2 activity measured in human CSF appears to be primarily due to sPLA2 activity.

Stock solutions and serial dilutions of PLA2 inhibitors ($AACOCF_3$, BEL and Thioetheramide-PC) were prepared in PLA2 assay buffer supplemented by 4.25 mM Triton X-100. Each assay was carried out in the absence or presence of 5 µL of the appropriate inhibitor.

Example 3

To determine if CSF sPLA2 activity is age or gender dependent, its normal physiologic levels were assessed from 32 healthy volunteers, as shown in Table 1.

TABLE 1

| Variable | Healthy Subjects (n = 32) |
| --- | --- |
| Gender (females/males) | 16/16 |
| Age (years) | 52.3 ± 15.2 |
| MMSE score | 29.5 ± 0.5 |
| sPLA2 activity (ΔFI/min) | 3.8 ± 1.0 |

Figure 4A:
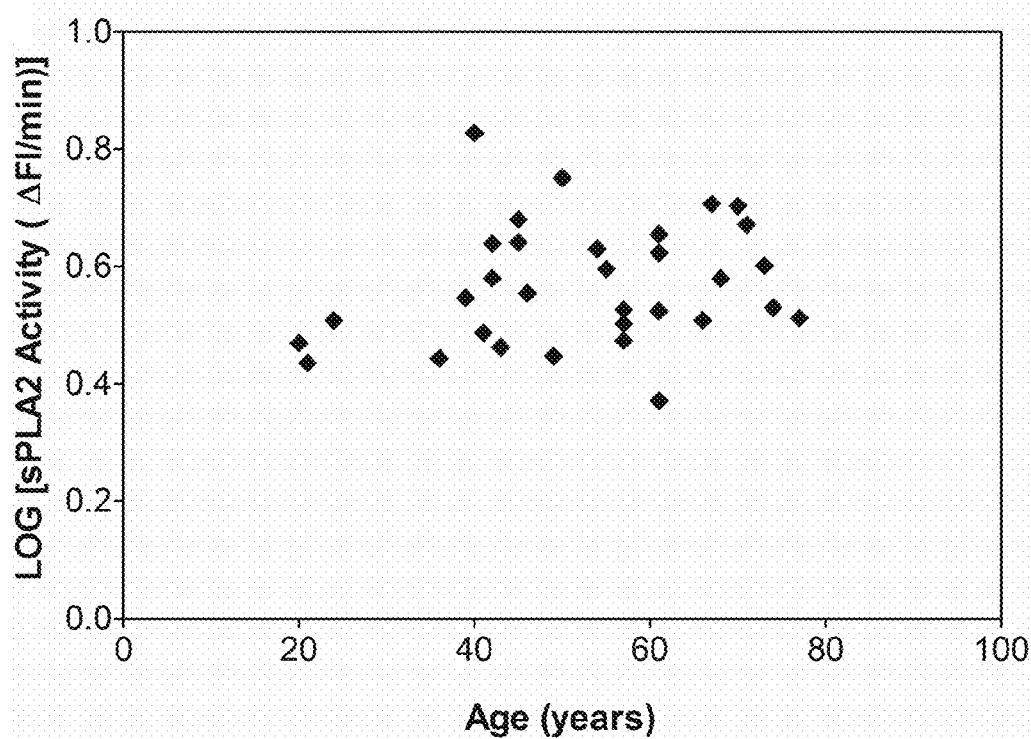
FIG. 4A is a scatter plot of CSF sPLA2 as a function of age.
Figure 4B:
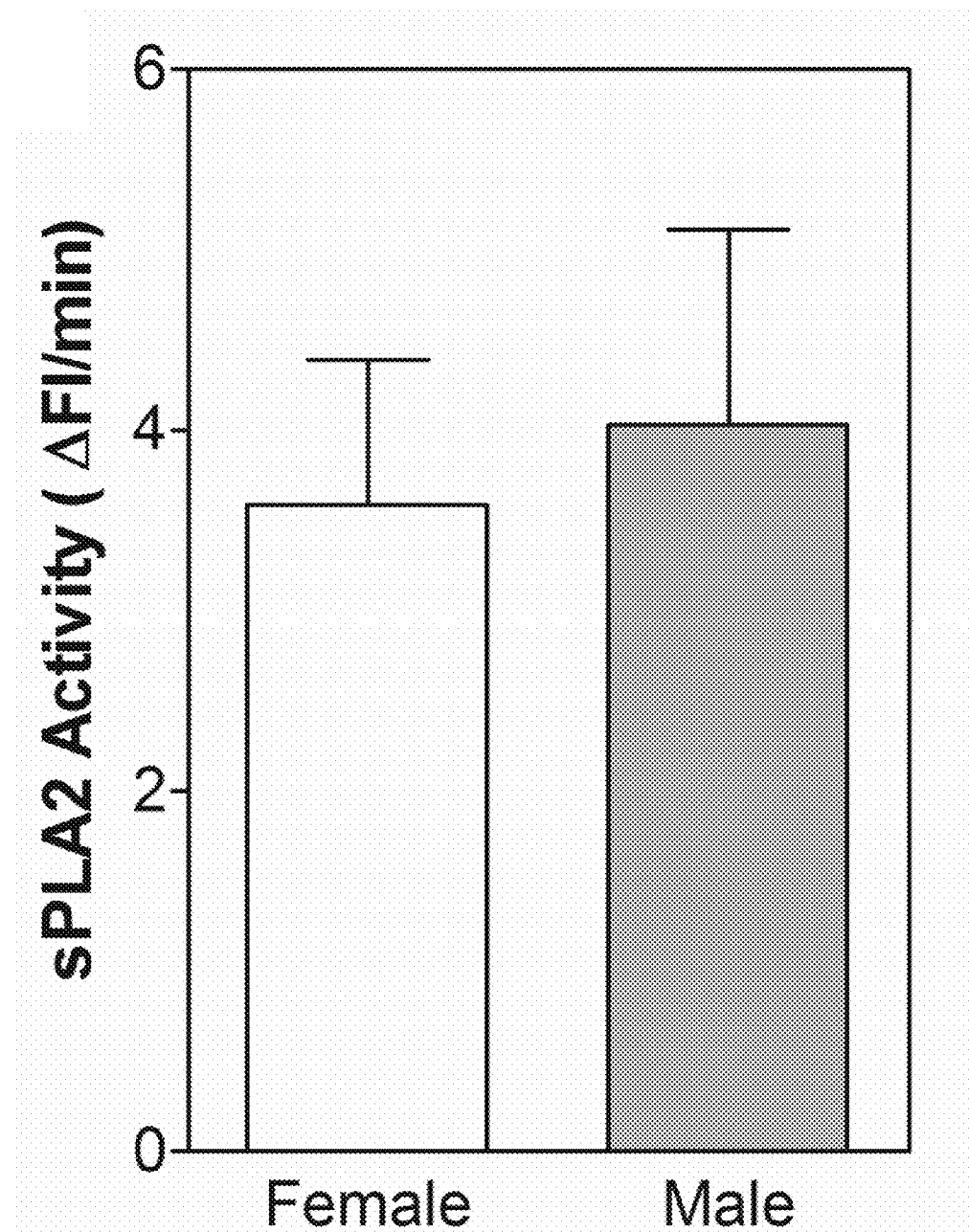
FIG. 4B is a graph of CSF sPLA2 activity as a function of gender.

As shown in FIG. 4A, sPLA2 activity in CSF does not seem to correlate to age (r=0.214; p=0.239; 95% CI−0.145 to 0.524). Moreover, no significant difference of sPLA2 activity was noticed between males and females, as shown in FIG. 4B ($t_{df+}=1.312$, p=0.200).

Statistical analyses were performed with Statgraphics® Centurion XV (StatPoint®, Herndon, Va.) and Graph Prism 3.0 (GraphPad Software™, San Diego, Calif.). A failure in the normal distribution of a variable was considered when values of Skewness and Kurtosis were outside of the range −2 to +2. If a variable was not normally distributed, a logarithmic transformation followed by a parametric test was performed. Differences between two means were assessed with unpaired, two-tailed Student's t-test. Correlations were analyzed statistically using Pearson's correlation test. The level of significance was defined as p<0.05.

Example 4

Since sPLA2s are known to be associated with systemic inflammatory, autoimmune, or allergic diseases and to play a key role in neuroinflammation, an investigation was conducted to determine whether the sPLA2 activity in human CSF might reflect an ongoing neuroinflammatory process. For this purpose, sPLA2 activity in multiple sclerosis ("MS") patients was measured. MS is a well-known chronic inflammatory disease of the central nervous system characterized by destruction of myelin sheaths and axonal loss.

Although no significant difference ($t_{df=40}$=0.607, p=0.548) of sPLA2 activity between MS and age-matched healthy controls was found, a significant and positive correlation between sPLA2 activity and $Q_{Alb}$ in age-matched healthy control (r=0.590; p<0.005; 95% CI: 0.212-0.814) as well as in MS (r=0.870; p<0.0001; 95% CI: 0.670-0.953) cases was observed, as shown in Table 2. Moreover, neither a significant difference in $Q_{Alb}$ between multiple sclerosis and age-matched healthy controls nor a significant correlation between age and sPLA2 activity or $Q_{Alb}$ were observed. These results suggest a strong correlation of the CSF sPLA2 activity with the degree of blood—CSF barrier (BCB) function as measured by $Q_{Alb}$.

TABLE 2

| | Healthy Control (n = 24) | Multiple Sclerosis (n = 18) | Statistical Analysis | |
|---|---|---|---|---|
| | | | Statistical Value | p Value |
| Demographic, clinical and biochemical features | | | | |
| Gender (Male) | 10 (42%) | 2 (11%) | N/A | 0.041 |
| Age (years) | 46.1 ± 12.3 | 41.6 ± 8.9 | z = −1.868 | 0.063 |
| Oligoclonal bands | 0 (0%) | 18 (100%) | N/A | <0.0001 |
| $Q_{Alb}$ | 4.7 ± 2.2 | 4.5 ± 1.4 | $t_{(df=36)}$ = 0.096 | 0.924 |
| sPLA2 activity (ΔFI/min) | 3.7 ± 1.0 | 3.8 ± 0.8 | $t_{(df=40)}$ = 0.607 | 0.548 |
| Pearson Correlation between $Q_{Alb}$ and sPLA2 activity | | | | |
| Pearson coefficient | 0.590 | 0.870 | | |
| p Value | <0.005 | <0.0001 | | |
| 95% CI | 0.212-0.814 | 0.670-0.953 | | |

According to the upper reference limit for $Q_{Alb}$ (6.8 for individuals under 45 years of age and 10.2 for individuals over 45 years of age), only 2 out of the 42 cases (5%) in the study were found to have a BCB dysfunction independently of their clinical diagnoses. Even when these two cases were removed from data analysis, the positive correlation between CSF sPLA2 activity and $Q_{Alb}$ remains in age-matched healthy controls (r=0.464; p=0.039; 95% CI: 0.027-0.752) and in MS (r=0.859; p<0.0001; 95% CI: 0.633-0.950) as well as in total population (r=0.602; p<0.0001; 95% CI: 0.341-0.777). Thus, independent of the clinical diagnoses and when no BCB impairment is observed, sPLA2 activity is strongly and positively correlated to $Q_{Alb}$.

In this EXAMPLE, venous puncture was performed to collect serum and CSF was obtained by lumbar puncture from the L3/L4 or L4/L5 intervertebral space. The first 12 mL of CSF were collected, centrifuged at 2000×g for 10 min at 4° C. and then aliquoted in 1 ml polypropylene tubes. All samples were sent in dry ice from Sahlgrenska University Hospital to New York State Institute for Basic Research, and were aliquoted once again to minimize freeze/thaw steps and finally kept at −80° C. until used. In summary, $Q_{Alb}$ determination and oligoclonal IgG-bands identification were used to evaluate the BCB integrity and as an indicator in the diagnosis of multiple sclerosis, respectively. While $Q_{Alb}$ was calculated as CSF albumin (mg/L)/serum albumin (g/L), identification of CSF-enriched oligoclonal IgG-bands was based on a cutoff level of two or more IgG bands.

Statistical analyses were performed using Statgraphics Centurion XV (StatPoint, Herndon, Va.) and Graph Prism 3.0. A failure in the normal distribution of a variable was considered when values of Skewness and Kurtosis were outside of the range −2 to +2. If a variable was not normally distributed, a logarithmic transformation followed by a parametric test or a non-parametric test was performed. Frequency distributions were compared with Fisher's test. Differences between two means were assessed with unpaired, two-tailed Student's t-test or Mann-Whitney's test. Correlations were analyzed statistically using Pearson's correlation test or Spearman's rank correlation test. The level of significance was defined as p<0.05.

Example 5

Figure 5A:
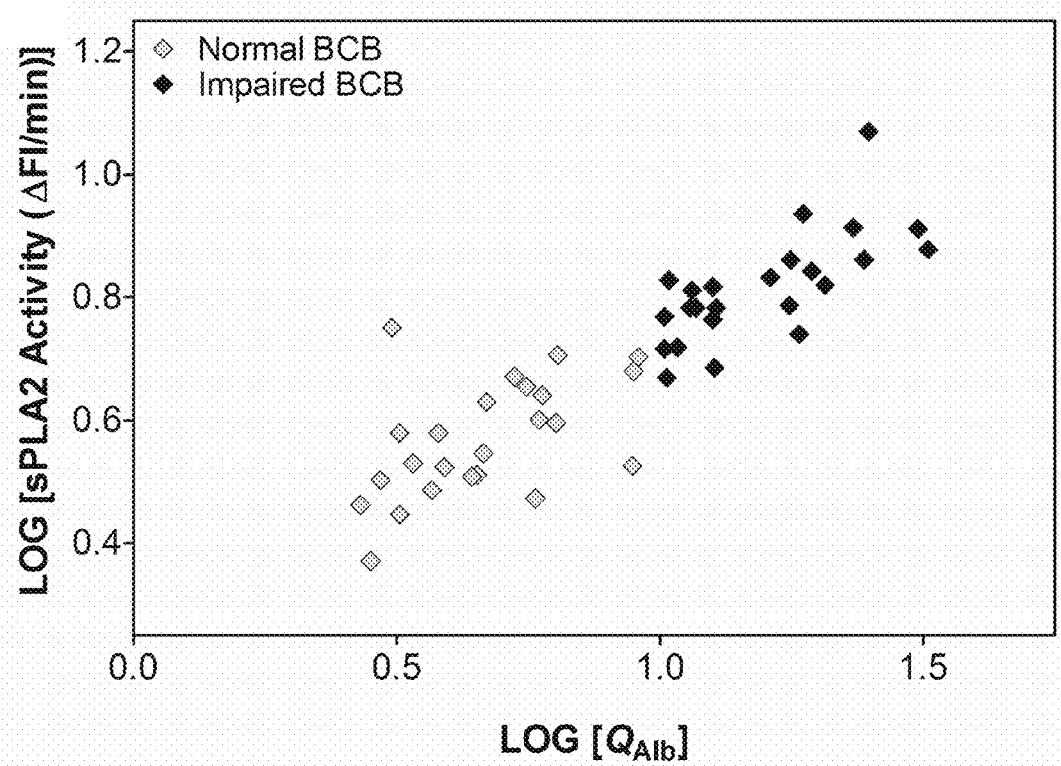
FIGS. 5A-5D are a series of graphs showing a comparison between sPLA2 activity and $Q_{Alb}$ in patients with normal or impaired BCB and an efficient discrimination between normal BCB and impaired BCB by CSF sPLA2 activity.

To determine if the positive correlation between sPLA2 activity and $Q_{Alb}$ is also applicable in BCB impaired cases, this relation was examined in a set of patients with and without BCB dysfunction. As expected, a significant difference in both sPLA2 activity and $Q_{Alb}$ between impaired BCB and age-matched normal BCB groups was found, as shown in Table 3. Moreover, while a significant and positive correlation between sPLA2 activity and $Q_{Alb}$ in age-matched normal BCB (r=0.516; p=0.0099; 95% CI: 0.142-0.761) and impaired BCB (r=0.710; p=0.0001; 95% CI: 0.429-0.865) groups as well as in the total population (r=0.877; p<0.0001; 95% CI: 0.790-0.930) cases was observed (FIG. 5A), no significant correlation between sPLA2 activity or $Q_{Alb}$ with age was detected. Thus, sPLA2 activity is strongly correlated to $Q_{Alb}$ independent of the age and of the BCB condition. These results suggest that like $Q_{Alb}$, sPLA2 activity measurement can evaluate BCB impairment.

TABLE 3

| | BCB Normal (n = 24) | BCB Impaired (n = 24) | Statistical Analysis | |
|---|---|---|---|---|
| | | | Statistical Value | p Value |
| Gender (Male) | 11 (46%) | 16 (67%) | N/A | 0.244 |
| Age (years) | 57.6 ± 11.5 | 63.7 ± 17.5 | z = −1.876 | 0.062 |
| $Q_{Alb}$ | 5.0 ± 1.9 | 16.7 ± 6.6 | $t_{(df=46)}$ = 11.46 | <0.0001 |
| sPLA2 activity (ΔFI/min) | 3.8 ± 0.8 | 6.7 ± 1.5 | $t_{(df=46)}$ = 9.261 | <0.0001 |

Figure 5B:
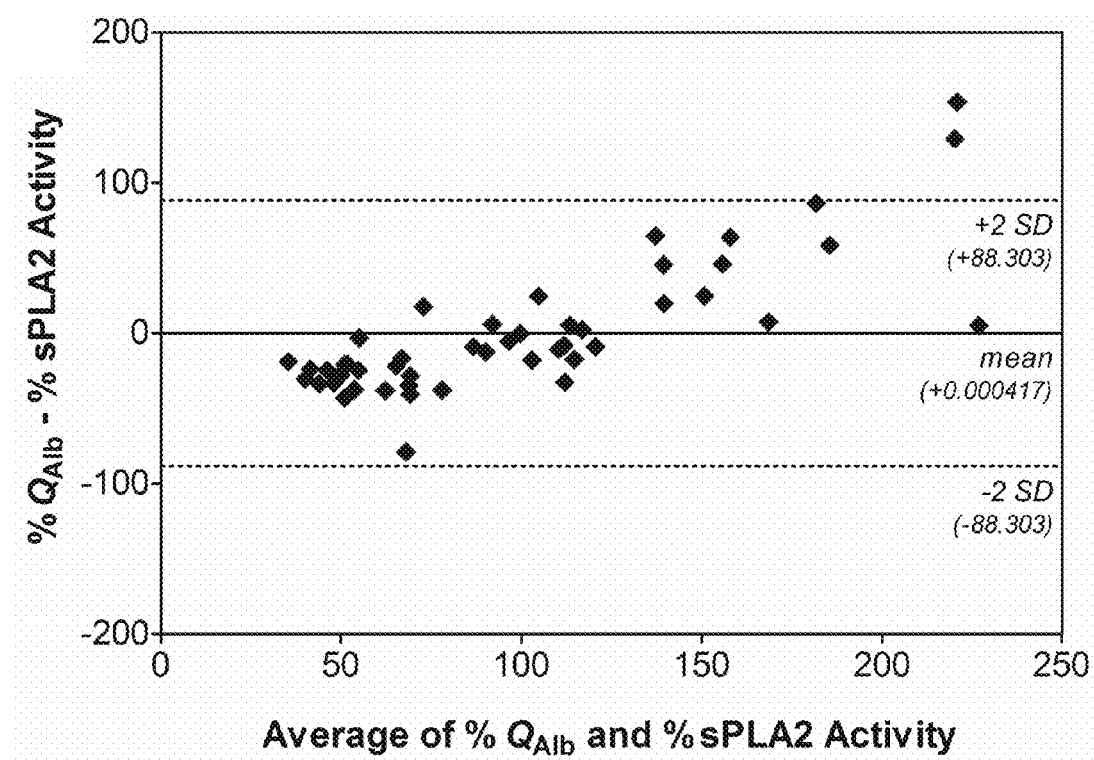
Figure 5C:
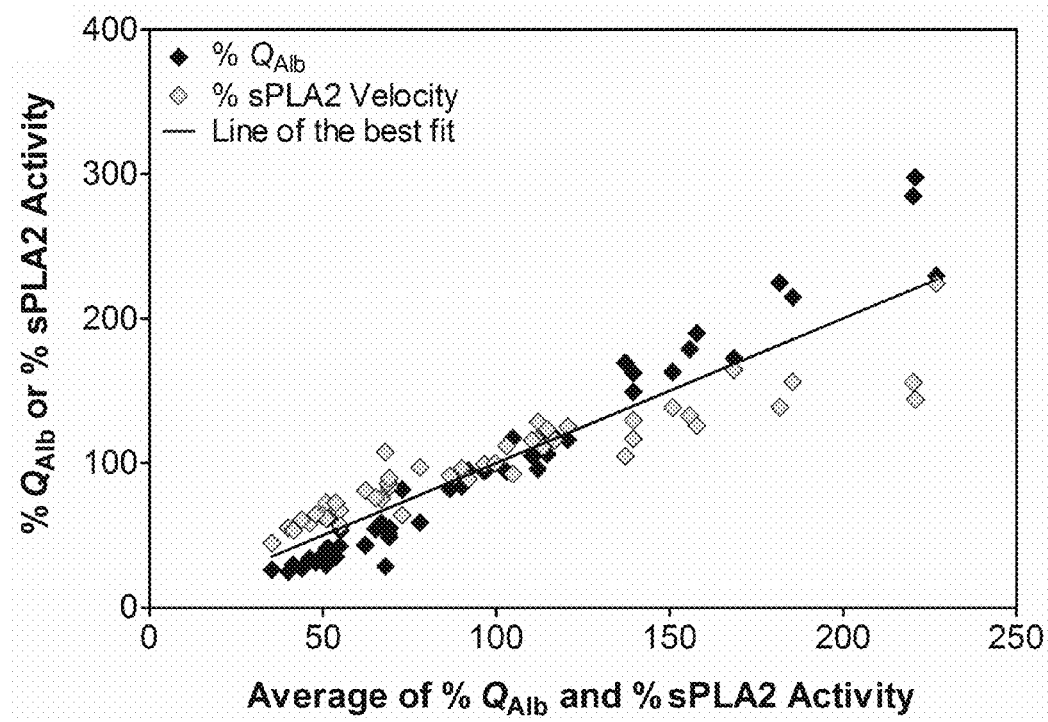

The strength of the new method was evaluated by assessing the agreement between the $Q_{Alb}$ and sPLA2 activity using the Bland-Altman and Sotgia methods, which allow calculation of the limits of agreement as well as identification of systematic errors and graphical visualization of the difference in magnitude between two analytical methods, respectively. The Bland-Altman plot is shown in FIG. 5B. The difference between % $Q_{Alb}$ and % sPLA2 activity measurement was plotted against the % mean from both methods and for each sample measured. The systematic difference between the two assay methods as calculated by the Bland-Altman analysis was <0.001. The two methods agreed fairly well for $Q_{Alb}$ values<24.9 and only 4.2% of the patients had value that differed by >2 SD. Since agreement between two methods is generally acceptable if <5% of values differ by >2 SD, the two approaches are considered equivalent in evaluating BCB impairment. Moreover, the Sotgia analysis showed that the values from sPLA2 activity measurement were higher and lower than the values from $Q_{Alb}$ at low and high levels of $Q_{Alb}$, respectively, as shown in FIG. 5C. Thus, it seems that the measurement of sPLA2 activity in CSF is a more sensitive approach than the evaluation of $Q_{Alb}$.

Figure 5D:
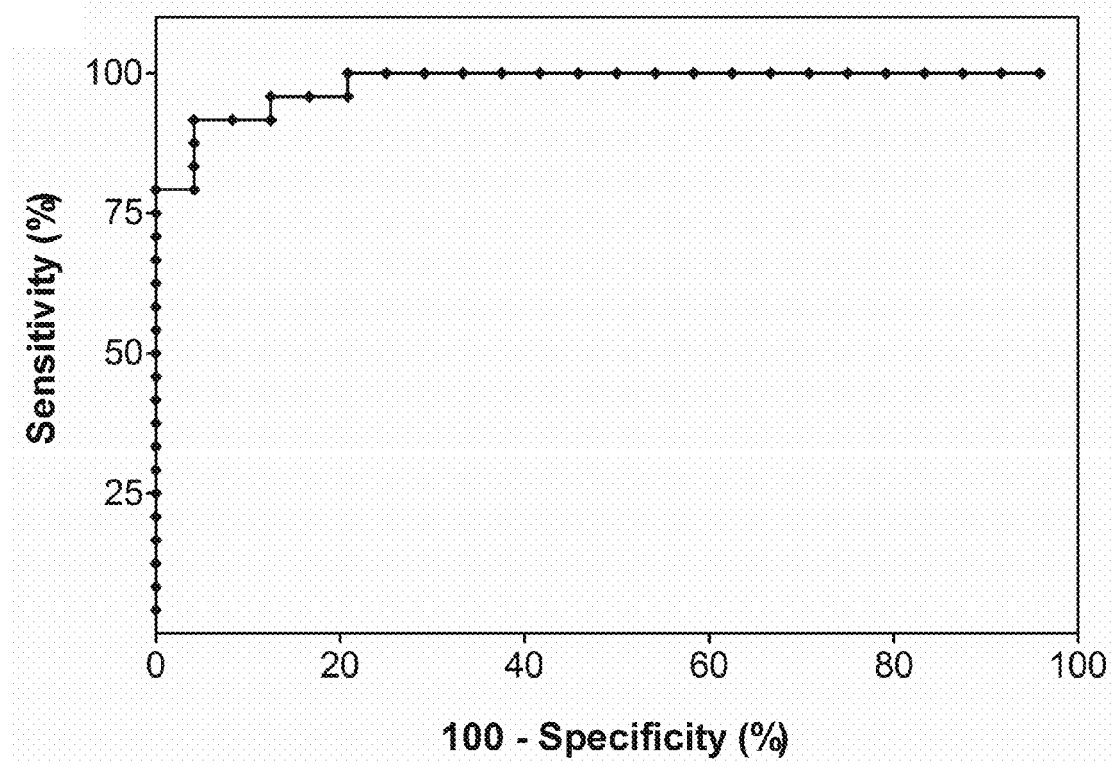

To evaluate the discrimination power of sPLA2 activity measurement a ROC analysis was performed. The results are shown in FIG. 5D. The analysis indicated that sPLA2 velocity efficiently discriminates normal BCB from impaired BCB (AUC=0.9809; 95% CI: 0.95-1.01). Furthermore with a cutoff value of 5.146 ΔFI/min, the sensitivity and specificity were 91.67% (95% Cl: 73.00-98.97) and 95.83% (95% Cl: 78.88-99.89), respectively. Thus, sPLA2 activity measurement in CSF provides a new sensitive and simple approach to evaluate the BCB integrity.

For the current EXAMPLE, statistical analyses were performed using Statgraphics Centurion XV (StatPoint, Herndon, Va.) and Graph Prism 3.0 (GraphPad software, San Diego, Calif.). Normal distribution was assessed using Skewness and Kurtosis. If a variable was not normally distributed, a parametric test followed by a logarithmic transformation or a non-parametric test was performed. Frequency distributions were compared with Fisher's test. Differences between two means were assessed with unpaired, two-tailed Student's t-test or Mann-Whitney's test. Correlations were analyzed statistically using Pearson's correlation test or Spearman's rank correlation test. Bland-Altman curves and Sotgia curves were constructed for comparison between $Q_{Alb}$ and sPLA2 activity assays. While Bland-Altman analysis allows to calculate limits of agreement and systematic errors, Sotgia approach allows to visualize graphically the difference in magnitude between two analytical methods. To minimize the unit difference and to perform both analyses, variables were normalized to the average of all values of the corresponding parameters and converted to percentage. Receiver operating characteristic (ROC) analysis was used to calculate sensitivity, specificity and cutoff values of considered biomarkers in selected groups. The optimal cutoff value was defined at the optimal combination of sensitivity and specificity. The level of significance was defined as $p<0.05$ The present invention has numerous uses, including but not limited to the following: (i) increased specificity in the differential diagnosis of neurodegenerative disorders; (ii) identification of neurological disorders which are not yet known to be associated with a blood-neural barrier impairment; (ii) classification of neurological disorders subgroups based on their level of BNB impairment as measured by CSF sPLA2 activity; (iii) assessment of BBB and/or BCB permeability in central nervous system disorders to monitor time-dependent response to therapies that target BNB disruption, as well as disease progression; (iv) identification of potential therapeutic windows to increase drug efficacy; and (v) increased understanding of the morphological and physiological nature of blood-neural barriers in developing, mature, and aging brains as well as their critical role in the pathophysiology of neurological disorders.

Although the present invention has been described in connection with a preferred embodiment, it should be understood that modifications, alterations, and additions can be made to the invention without departing from the scope of the invention.

What is claimed is:

1. A method for evaluating the permeability of a blood-neural barrier, the method comprising the steps of:
   exposing a sample of cerebrospinal fluid to a probe having a continuous fluorescence response to secretory Ca2+-dependent phospholipase A activity;
   detecting a change in said fluorescence response over time; and
   determining the permeability of the blood-neural barrier based on the change in said fluorescence response.

2. The method of claim 1, wherein said probe is incorporated into a liposome.

3. The method of claim 2, wherein said probe comprises 1,2-bis-(4,4-difluoro-5,7-dimethyl-4-bora-3a,4a-diaza-s-indacene-3-undecanoyl)-sn-glycero-3-phosphocholine.

4. The method of claim 2, wherein said probe is quenched before it is exposed to the sample of cerebrospinal fluid.

5. The method of claim 1, wherein the step of determining the permeability of the blood-neural barrier comprises comparing the change in said fluorescence response to healthy controls.

6. The method of claim 1, wherein said sample of cerebrospinal fluid is from a patient diagnosed with a neurological disorder.

7. A method for diagnosing impaired permeability of a patient's blood-neural barrier from a sample of cerebrospinal fluid taken from said patient, the method comprising the steps of:
   exposing a sample of cerebrospinal fluid to a probe having a continuous fluorescence response to secretory Ca2+-dependent phospholipase A activity;
   detecting a change in said fluorescence response over time; and
   determining the permeability of the blood-neural barrier based on the change in said fluorescence response;
   diagnosing the presence of impaired permeability of the patient's blood-neural barrier on the change in said fluorescence response.

8. The method of claim 7, wherein said probe is incorporated into a liposome.

9. The method of claim 7, wherein said probe comprises 1,2-bis-(4,4-difluoro-5,7-dimethyl-4-bora-3a,4a-diaza-s-indacene-3-undecanoyl)-sn-glycero-3-phosphocholine.

10. The method of claim 7, wherein the step of determining the permeability of the blood-neural barrier comprises comparing the change in said fluorescence response to healthy controls.

11. The method of claim 7, further comprising the step of:
    diagnosing a neurological disorder in said patient based on the presence of impaired permeability of the patient's blood-neural barrier.

* * * * *